(12) United States Patent
Schelberger et al.

(10) Patent No.: US 6,344,469 B1
(45) Date of Patent: Feb. 5, 2002

(54) FUNGICIDE MIXTURES

(75) Inventors: Klaus Schelberger, Gönnheim; Reinhold Saur, Böhl-Iggelheim; Hubert Sauter, Mannheim; Bernd Müller, Frankenthal; Erich Birner, Altleiningen; Joachim Leyendecker, Ladenburg; Eberhard Ammermann, Heppenheim; Gisela Lorenz, Neustadt; Siegfried Strathmann, Limburgerhof, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/424,917

(22) PCT Filed: May 20, 1998

(86) PCT No.: PCT/EP98/02945

§ 371 Date: Dec. 1, 1999

§ 102(e) Date: Dec. 1, 1999

(87) PCT Pub. No.: WO98/54968

PCT Pub. Date: Dec. 10, 1998

(30) Foreign Application Priority Data

Jun. 4, 1997 (DE) .......................... 197 23 288

(51) Int. Cl.⁷ ................. A01N 43/82; A01N 43/64; A01N 43/56
(52) U.S. Cl. ................. 514/361; 514/384; 514/407
(58) Field of Search ................. 514/361, 384, 514/407

(56) References Cited

U.S. PATENT DOCUMENTS 4,931,581 A    6/1990   Schurter et al. ............. 560/18

FOREIGN PATENT DOCUMENTS

| WO | 96/01256 | 1/1996 |
|----|----------|--------|
| WO | 96/10258 | 1/1996 |
| WO | 96/03047 | 2/1996 |
| WO | 97/01277 | 1/1997 |

*Primary Examiner*—Allen J. Robinson
(74) *Attorney, Agent, or Firm*—Keil & Weinkauf

(57) ABSTRACT

Fungicidal mixture comprises
  a) a carbamate of the formula I,

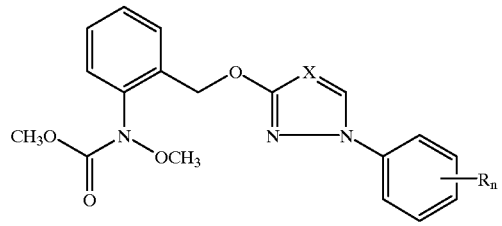

in which X is CH or N, n is 0, 1 or 2 and R is halogen, $C_1$–$C_4$-alkyl and $C_1$–$C_4$-haloalkyl, it being possible for the radicals R to be different if n is 2, or a salt or adduct thereof, and b) a 4,5-benzo-1-thia-2,3-diazole of the formula II

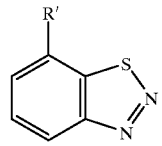

in which R' is CN, $CO_2H$, $CO_2$—$C_1$–$C_4$-alkyl or CO—S—$C_1$–$C_4$-alkyl, or a salt or adduct thereof, in a synergistically effective amount.

13 Claims, No Drawings

FUNGICIDE MIXTURES

This application is a 371 of PCT/EP98/02945, filed May 20, 1998.

The present invention relates to a fungicidal mixture which comprises a) a carbamate of the formula I,

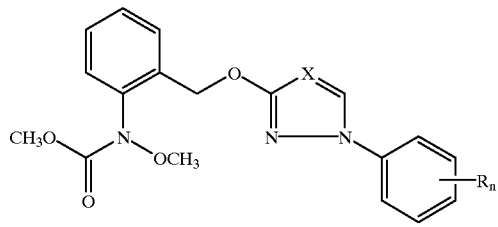

in which X is CH and N, n is 0, 1 or 2 and R is halogen, $C_1-C_4$-alkyl and $C_1-C_4$-haloalkyl, it being possible for the radicals R to be different if n is 2, or a salt or adduct thereof, and b) a 4,5-benzo-1-thia-2,3-diazole of the formula II

in which R' is CN, $CO_2H$, $CO_2-C_1-C_4$-alkyl or $CO—S—C_1-C_4$-alkyl, or a salt or adduct thereof, in a synergistically effective amount.

Moreover, the invention relates to methods for controlling harmful fungi using mixtures of the compounds I and II and to the use of the compound I and the compound II for preparing such mixtures.

The compounds of the formula I, their preparation and their activity against harmful fungi are disclosed in the literature (WO-A 96/01,256; WO-A 96/01,258).

Compounds of the formula II are disclosed in the literature as active compounds having immunizing effects on plants (EP-A 313 512). In addition, synergistic mixtures comprising the compounds II are disclosed (WO-A 97/01,277).

It is an object of the present invention to provide mixtures which have an improved activity against harmful fungi combined with a reduced total amount of active ingredients applied (synergistic mixtures), with a view to reducing the application rates and to improving the activity spectrum of the known compounds I and II.

We have found that this object is achieved by the mixture defined at the outset. Moreover, we have found that better control of harmful fungi is possible by applying the compound I and the compound II simultaneously together or separately or by applying the compound I and the compounds II in succession than when the individual compounds are used alone.

The formula I in particular represents carbamates in which the combination of the substituents corresponds to a row of the following table:

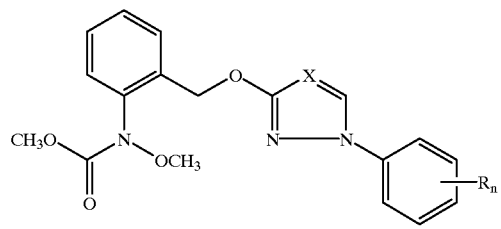

| No. | X | $R_n$ |
|---|---|---|
| I.1 | N | 2-F |
| I.2 | N | 3-F |
| I.3 | N | 4-F |
| I.4 | N | 2-Cl |
| I.5 | N | 3-Cl |
| I.6 | N | 4-Cl |
| I.7 | N | 2-Br |
| I.8 | N | 3-Br |
| I.9 | N | 4-Br |
| I.10 | N | 2-$CH_3$ |
| I.11 | N | 3-$CH_3$ |
| I.12 | N | 4-$CH_3$ |
| I.13 | N | 2-$CH_2CH_3$ |
| I.14 | N | 3-$CH_2CH_3$ |
| I.15 | N | 4-$CH_2CH_3$ |
| I.16 | N | 2-$CH(CH_3)_2$ |
| I.17 | N | 3-$CH(CH_3)_2$ |
| I.18 | N | 4-$CH(CH_3)_2$ |
| I.19 | N | 2-$CF_3$ |
| I.20 | N | 3-$CF_3$ |
| I.21 | N | 4-$CF_3$ |
| I.22 | N | 2,4-$F_2$ |
| I.23 | N | 2,4-$Cl_2$ |
| I.24 | N | 3,4-$Cl_2$ |
| I.25 | N | 2-Cl, 4-$CH_3$ |
| I.26 | N | 3-Cl, 4-$CH_3$ |
| I.27 | CH | 2-F |
| I.28 | CH | 3-F |
| I.29 | CH | 4-F |
| I.30 | CH | 2-Cl |
| I.31 | CH | 3-Cl |
| I.32 | CH | 4-Cl |
| I.33 | CH | 2-Br |
| I.34 | CH | 3-Br |
| I.35 | CH | 4-Br |
| I.36 | CH | 2-$CH_3$ |
| I.37 | CH | 3-$CH_3$ |
| I.38 | CH | 4-$CH_3$ |
| I.39 | CH | 2-$CH_2CH_3$ |
| I.40 | CH | 3-$CH_2CH_3$ |
| I.41 | CH | 4-$CH_2CH_3$ |
| I.42 | CH | 2-$CH(CH_3)_2$ |
| I.43 | CH | 3-$CH(CH_3)_2$ |
| I.44 | CH | 4-$CH(CH_3)_2$ |
| I.45 | CH | 2-$CF_3$ |
| I.46 | CH | 3-$CF_3$ |
| I.47 | CH | 4-$CF_3$ |
| I.48 | CH | 2,4-$F_2$ |
| I.49 | CH | 2,4-$Cl_2$ |
| I.50 | CH | 3,4-$Cl_2$ |
| I.51 | CH | 2-Cl, 4-$CH_3$ |
| I.52 | CH | 3-Cl, 4-$CH_3$ |

Particular preference is given to the compounds I.12, I.23, I.32 and I.38.

The formula II in particular represents 4,5-benzo-1-thia-2,3-diazoles in which R' corresponds to one of the groups in the following table:

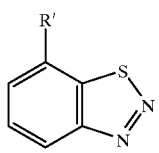

II

| No. | R' |
|---|---|
| II.1 | CN |
| II.2 | CO$_2$H |
| II.3 | CO$_2$CH$_3$ |
| II.4 | CO—SCH$_3$ |

Particular preference is given to the compound II.4.

Owing to the basic character of their nitrogen atoms, the compounds I and II are capable of forming salts or adducts with inorganic or organic acids or with metal ions.

Examples of inorganic acids are hydrohalic acids such as hydrofluoric acid, hydrochloric acid, hydrobromic acid and hydriodic acid, and furthermore sulfuric acid, phosphoric acid and nitric acid.

Suitable organic acids are, for example, formic acid and alkanoic acids, such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulfonic acids (sulfonic acids having straight-chain or branched alkyl radicals of 1 to 20 carbon atoms), arylsulfonic acids or aryldisulfonic acids (aromatic radicals, such as phenyl and naphthyl, which carry one or two sulfo groups), alkylphosphonic acids (phosphonic acids having straight-chain or branched alkyl radicals of 1 to 20 carbon atoms), arylphosphonic acids or aryldiphosphonic acids (aromatic radicals, such as phenyl and naphthyl, which carry one or two phosphoric acid radicals), it being possible for the alkyl or aryl radicals to carry further substituents, e.g. p-toluenesulfonic acid, salicylic acid, p-aminosalicylic acid, 2-phenoxybenzoic acid, 2-acetoxybenzoic acid, etc.

Suitable metal ions are, in particular, the ions of the elements of the first to eighth sub-group, in particular chromium, manganese, iron, cobalt, nickel, copper, zinc, and furthermore of the second main group, in particular calcium and magnesium, and of the third and fourth main group, in particular aluminum, tin and lead. The metals can exist in the various valences which they can assume.

Particularly preferred salts of the compound II.2 are alkali metal and alkaline earth metal salts (in particular lithium salts, sodium salts, potassium salts, magnesium salts and calcium salts), and organic salts, especially of ammonium ions or of the ions of primary, secondary and tertiary amines (in particular trimethylamine, triethylamine, N,N-dimethylaniline, pyridine, triethanolamine, piperidine and morpholine).

When preparing the mixtures, it is preferred to employ the pure active ingredients I and II, to which further active ingredients against harmful fungi or other pests, such as insects, arachnids and nematodes or else herbicidal or growth-regulating active ingredients or fertilizers can be admixed.

The mixtures of the compounds I and II, or the simultaneous joint or separate use of the compounds I and II, exhibit outstanding activity against a wide range of phytopathogenic fungi, in particular from the class of the Ascomycetes, Basidiomycetes, Phycomycetes and Deuteromycetes. Some of them act systemically and can therefore be employed as foliar- and soil-acting fungicides.

They are especially important for controlling a large number of fungi in a variety of crop plants such as cotton, vegetable species (e.g. cucumbers, beans, tomatoes, potatoes and cucurbits), barley, grass, oats, bananas, coffee, maize, fruit species, rice, rye, soya, grapevine, wheat, ornamentals, sugarcane, and a variety of seeds.

They are particularly suitable for controlling the following phytopathogenic fungi: *Erysiphe graminis* (powder mildew) in cereals, *Erysiphe cichoracearum* and Sphaerotheca fuliginea in cucurbits, *Podosphaera leucotricha* in apples, Uncinula necator in grapevines, Puccinia species in cereals, Rhizoctonia species in cotton, rice and lawns, Ustilago species in cereals and sugarcane, Venturia inaequalis (scab) in apples, Helminthosporium species in cereals and lawns, *Septoria nodorum* in wheat, *Botrytis cinerea* (gray mold) in strawberries, vegetables, ornamentals and grapevines, Sclerotina species in rape-seed and lawns, *Cercospora arachidicola* in groundnuts, Pseudocercosporella herpotrichoides in wheat and barley, *Pyricularia oryzae* in rice, *Phytophthora infestans* in potatoes and tomatoes, Pythium species in ornamentals, vegetables and lawns, *Plasmopara viticola* in grapevines, Pseudoperonospora species in hops and cucumbers, Alternaria species in vegetables and fruit, Mycosphaerella species in bananas and Fusarium- and Verticillium species.

Furthermore, they can be used in the protection of materials (e.g. in the protection of wood), for example against *Paecilomyces variotii*.

The compounds I and II can be applied simultaneously, either together or separately, or in succession, the sequence, in the case of separate application, generally not having any effect on the result of the control measures.

The compounds I and II are usually used in a weight ratio of 10:1 to 0.01:1, preferably from 5:1 to 0.05:1, in particular 1:1 to 0.05:1.

Depending on the kind of effect desired, the application rates of the mixtures according to the invention are, in particular in agricultural crops, from 0.01 to 8 kg/ha, preferably 0.1 to 5 kg/ha, in particular 0.5 to 3.0 kg/ha.

The application rates for the compounds I are from 0.01 to 1.0 kg/ha, preferably 0.05 to 0.8 kg/ha, in particular 0.05 to 0.5 kg/ha.

Correspondingly, in the case of the compounds II, the application rates are from 0.001 to 1.0 kg/ha, preferably 0.01 to 0.5 kg/ha, in particular 0.01 to 0.3 kg/ha.

For seed treatment, the application rates of the mixture are generally from 0.001 to 250 g/kg of seed, preferably 0.01 to 100 g/kg, in particular 0.01 to 50 g/kg.

If phytopathogenic harmful fungi are to be controlled, the separate or joint application of the compounds I and II or of the mixtures of the compounds I and II is effected by spraying or dusting the seeds, the plants or the soils before or after sowing of the plants, or before or after plant emergence.

The fungicidal synergistic mixtures according to the invention, or the compounds I and II, can be formulated for example in the form of ready-to-spray solutions, powders and suspensions or in the form of highly concentrated aqueous, oily or other suspensions, dispersions, emulsions, oil dispersions, pastes, dusts, materials for broadcasting or granules, and employed by spraying, atomizing, dusting, broadcasting or watering. The use form depends on the intended purpose; in any case, it should guarantee as fine and uniform as possible a distribution of the mixture according to the invention.

The formulations are prepared in a manner known per se, e.g. by adding solvents and/or carriers. It is usual to admix inert additives such as emulsifiers or dispersants, with the formulations.

Suitable surfactants are the alkali metal salts, alkaline earth metal salts and ammonium salts of aromatic sulfonic acids, e.g. ligno-, phenol-, naphthalene- and dibutylnaphthalenesulfonic acid, and of fatty acids, alkyl- and alkylarylsulfonates, alkyl, lauryl ether and fatty alcohol sulfates, and salts of sulfated hexa-, hepta- and octadecanols, or of fatty alcohol glycol ethers, condensates of sulfonated naphthalene and its derivatives with formaldehyde, condensates of naphthalene or of the naphthalene sulfonic acids with phenol and formaldehyde, polyoxyethylene octylphenol ether, ethoxylated isooctyl-, octyl- or nonylphenol, alkylphenol polyglycol ethers, tributylphenyl polyglycol ethers, alkylarylpolyether alcohols, isotridecyl alcohol, fatty alcohol-ethylene oxide condensates, ethoxylated castor oil, polyoxyethylene alkyl ethers or polyoxypropylene alkyl ethers, lauryl alcohol polyglycol ether acetate, sorbitol esters, lignosulf ite waste liquors or methylcellulose.

Powders, materials for broadcasting and dust can be prepared by mixing or jointly grinding the compounds I or II or the mixture of the compounds I and II with a solid carrier.

Granules (e.g. coated granules, impregnated granules or homogeneous granules) are usually prepared by binding the active ingredient, or active ingredients, to a solid carrier.

Fillers or solid carriers are, for example, mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, and fertilizers, such as ammonium sulfate, ammonium phosphate, ammonium nitrate, ureas, and products of vegetable origin, such as cereal meal, tree bark meal, wood meal and nutshell meal, cellulose powders or other solid carriers.

The formulations generally comprise from 0.1 to 95% by weight, preferably 0.5 to 90% by weight, of one of the compounds I or II or of the mixture of the compounds I and II. The active ingredients are employed in a purity of from 90% to 100%, preferably 95% to 100% (according to NMR spectrum or HPLC).

The compounds I or II, or the mixtures, or the corresponding formulations, are applied by treating the harmful fungi, their habitat, or the plants, seeds, soils, areas, materials or spaces to be kept free from them with a fungicidally effective amount of the mixture, or of the compounds I and II in the case of separate application.

Application can be effected before or after infection by the harmful fungi.

USE EXAMPLE 1

Protective Activity Against Powdery Mildew of Wheat

Leaves of potted wheat seedlings cv. "Frühgold" were sprayed to runoff point with an aqueous preparation of active ingredient which had been prepared from a stock solution comprising 10% of active ingredient, 63% of cyclohexanone and 27% of emulsifier. After a 7-day cultivation in a greenhouse at from 20 to 24° C. and from 60 to 90% relative atmospheric humidity, the plants were dusted with spores of powdery mildew of wheat (Erysiphe graminis forma specialis tritici). The test plants were subsequently placed in a greenhouse at from 20 to 24° C. and from 60 to 90% relative atmospheric humidity. After a further 7 days, the extent of mildew development was determined visually as % infection of the total leaf area.

The evaluation was carried out by determining the infected leaf areas in percent. These percentages were converted into efficacies. The efficacy (E) was calculated as follows using Abbot's formula:

$$E=(1-\alpha)\cdot 100/\beta$$

α corresponds to the fungal infection of the treated plants in % and

β corresponds to the fungal infection of the untreated (control) plants in %

An efficacy of 0 means that the infection level of the treated plants corresponds to that of the untreated control plants; an efficacy of 100 means that the treated plants were not infected.

The expected efficacies of the mixtures of the active ingredients were determined using Colby's formula [R. S. Colby, Weeds 15, 20–22 (1967)] and compared with the observed efficacies.

Colby's formula: $E=x+y-x\cdot y/100$

E expected efficacy, expressed in % of the untreated control, when using the mixture of the active ingredients A and B at the concentrations a and b x efficacy, expressed in % of the untreated control, when using active ingredient A at a concentration of a y efficacy, expressed in % of the untreated control, when using active ingredient B at a concentration of b The results are shown in Tables 3 and 4.

TABLE 3

| Ex. | Active ingredient | Concentration of active ingredient in the spray liquor in ppm | Efficacy in % of the untreated control |
|---|---|---|---|
| 1 C | Control (untreated) | (100% infection) | 0 |
| 2 C | Compound I.32 | 1 | 70 |
|  |  | 0.25 | 10 |
| 3 C | Compound II.4 | 10 | 30 |
|  |  | 2.5 | 10 |

TABLE 4

| Ex. | Mixture according to the invention | Observed efficacy | Calculated efficacy*) |
|---|---|---|---|
| 4 | 1 ppm I.32 + 10 ppm II.4 | 95 | 79 |
| 5 | 0.25 ppm I.32 + 2.5 ppm II.4 | 40 | 19 |

USE EXAMPLE 2

Protective Activity Against *Phytophthora Infestans* on Tomatoes

Leaves of potted plants cv. "GroBe Fleischtomate" were sprayed to runoff point with an aqueous suspension which had been prepared from a stock solution comprising 10% of active ingredient, 63% of cyclohexanone and 27% of emulsifier. After 7 days, the leaves were inoculated with an aqueous zoospore suspension of Phytophthora infestans. The plants were subsequently placed in a water vapor-saturated chamber at from 16 to 18° C. After a further 6 days, the tomato blight on the untreated, but infected control plants had developed to such an extent that the infection could be determined visually in %.

Evaluation was carried out as described for Use Example 1.

The results are shown in Tables 5 and 6 below.

TABLE 5

| Ex. | Active ingredient | Concentration of active ingredient in the spray liquor in ppm | Efficacy in % of the untreated control |
|---|---|---|---|
| 6 C | Control (untreated) | (97% infection) | 0 |
| 7 C | Compound I.32 | 1 | 60 |
|  |  | 0.25 | 48 |
| 8 C | Compound II.4 | 10 | 28 |
|  |  | 2.5 | 17 |

TABLE 6

| Ex. | Mixture according to the invention | Observed efficacy | Calculated efficacy *) |
|---|---|---|---|
| 9 | 1 ppm I.32 + 10 ppm II.4 | 98 | 71 |
| 10 | 0.25 ppm I.32 + 2.5 ppm II.4 | 84 | 57 |

*) calculated using Colby's formula

The test results show that the observed efficacy in all mixing ratios is higher than the efficacy that had been calculated beforehand using Colby's formula.

We claim:

1. A fungicidal composition comprising a) a carbamate of formula I, in which X is CH or N, n is 0, 1 or 2 and R is halogen, $C_1$–$C_4$-alkyl and $C_1$–$C_4$-haloalkyl, wherein the radicals R are identical or different when n is 2, or a salt or adduct thereof, and b) a 4,5-benzo-1-thia-2,3-diazole compound of formula II in which R' is CN, $CO_2H$, $CO_2$–$C_1$–$C_4$-alkyl or CO—S—$C_1$–$C_4$-alkyl, or a salt or adduct thereof, in synergistically effective amounts and in a weight ratio of the carbamate of formula I or the salt or adduct thereof to the compound of formula II or the salt or adduct thereof of from 10:1 to 0.01:1.

2. The composition defined in claim 1, wherein the weight ratio of the carbamate of formula I or the salt or adduct thereof to the compound of formula II or the salt or adduct thereof is from 5:1 to 0.05:1.

3. The composition defined in claim 1 which is conditioned in two parts, one part comprising the carbamate of formula I or the salt or adduct thereof in a solid or liquid carrier, and the other part comprising the compound of formula II or the salt or adduct thereof in a solid or liquid carrier.

4. The composition defined in claim 1, wherein X is CH.

5. The composition defined in claim 1, wherein R denotes halogen.

6. The composition defined in claim 4, wherein R denotes halogen.

7. A method for controlling harmful fungi, which comprises treating the harmful fungi, their habitat, or plants, seeds, soils, areas, materials or spaces to be kept free from said fungi with synergistically effective amounts of a carbamate of formula I or a salt or adduct thereof and a compound of formula II, wherein the carbamate of formula I and the compound of formula II are as set forth in claim 1 and the carbamate or the salt or adduct thereof and the compound of formula II or the salt or adduct thereof are applied in a weight ratio of from 10:1 to 0.01:1.

8. The method of claim 7, wherein the carbamate of formula I or the salt or adduct thereof and the compound of formula II or the salt or adduct thereof are applied simultaneously together or separately, or in succession.

9. The method of claim 7, wherein the carbamate of formula I or the salt or adduct thereof is applied in an amount of from 0.01 to 1.0 kg/ha.

10. The method of claim 7, wherein the compound of formula II or the salt or adduct thereof is applied in an amount of from 0.001 to 1.0 kg/ha.

11. The method of claim 7, wherein X is CH.

12. The method of claim 7, wherein R denotes halogen.

13. The method of claim 11, wherein R denotes halogen.

* * * * *